(12) United States Patent
Kondo et al.

(10) Patent No.: US 7,387,982 B2
(45) Date of Patent: Jun. 17, 2008

(54) METHOD OF PRODUCING CATALYST FOR SYNTHESIS OF UNSATURATED ALDEHYDE AND UNSATURATED CARBOXYLIC ACID AND CATALYST PREPARED BY THIS METHOD

(75) Inventors: Masahide Kondo, Hiroshima (JP); Seiichi Kawato, Hiroshima (JP); Toru Kuroda, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/495,871

(22) PCT Filed: Dec. 25, 2002

(86) PCT No.: PCT/JP02/13519

§ 371 (c)(1),
(2), (4) Date: May 18, 2004

(87) PCT Pub. No.: WO03/057366

PCT Pub. Date: Jul. 17, 2003

(65) Prior Publication Data

US 2004/0267048 A1    Dec. 30, 2004

(30) Foreign Application Priority Data

Dec. 28, 2001    (JP) .............................. 2001-399308

(51) Int. Cl.
*B01J 23/00* (2006.01)
(52) U.S. Cl. ..................................... 502/311; 502/316
(58) Field of Classification Search ................ 502/305, 502/311, 316, 321; 264/464, 176.1, 219, 264/239
See application file for complete search history.

(56) References Cited

U.S. PATENT DOCUMENTS

| | | | |
|---|---|---|---|
| 4,008,179 A * | 2/1977 | Gasson et al. | 502/209 |
| 4,558,028 A * | 12/1985 | Tsuneki et al. | 502/211 |
| 4,939,260 A * | 7/1990 | Inoue et al. | 546/286 |
| 5,072,052 A | 12/1991 | Boeck et al. | |
| 6,171,998 B1 * | 1/2001 | Lee et al. | 502/304 |
| 6,479,691 B1 * | 11/2002 | Sasaki et al. | 558/321 |
| 6,514,902 B1 * | 2/2003 | Inoue et al. | 502/305 |
| 6,583,316 B1 | 6/2003 | Onodera et al. | |
| 2004/0267048 A1 | 12/2004 | Kondo et al. | |

FOREIGN PATENT DOCUMENTS

| | | |
|---|---|---|
| CN | 1226462 A | 8/1999 |
| CN | 1280036 A | 1/2001 |
| EP | 1 052 017 A2 | 11/2000 |
| JP | 4-4048 | 1/1992 |
| JP | 7-016464 | 1/1995 |
| JP | 09-052053 | 2/1997 |
| JP | 10-71333 | 3/1998 |
| JP | 2000-071313 | 3/2000 |
| JP | 2003-10691 | 1/2003 |

OTHER PUBLICATIONS

U.S. Appl. No. 10/582,859, filed Jun. 14, 2006, Kondo et al.

* cited by examiner

*Primary Examiner*—Cam N. Nguyen
(74) *Attorney, Agent, or Firm*—Oblon, Spivak, McClelland, Maier & Neustadt, P.C.

(57) ABSTRACT

The method of producing a catalyst for synthesis of an unsaturated aldehyde and unsaturated carboxylic acid of the present invention is characterized in that the method comprises a step of adding liquid to particles containing molybdenum, bismuth and iron and kneading the mixture, and extrusion-molding this kneaded substance, a step of preserving the molded article obtained by extrusion molding, and at least one step of drying and calcining the preserved molded article, and the contact time of particles containing molybdenum, bismuth and iron with liquid is 1 to 48 hours, and the preserving time of the molded article is 50% or more of the contact time of particles containing molybdenum, bismuth and iron with liquid. According to the production method of the present invention, catalytic activity can be easily controlled, and a catalyst having high activity and high selectivity is obtained.

9 Claims, No Drawings

METHOD OF PRODUCING CATALYST FOR SYNTHESIS OF UNSATURATED ALDEHYDE AND UNSATURATED CARBOXYLIC ACID AND CATALYST PREPARED BY THIS METHOD

TECHNICAL FIELD

The present invention relates to a method of producing an extrusion molding catalyst containing at least molybdenum, bismuth and iron, used in subjecting propylene, isobutylene, tert-butyl alcohol (hereinafter, referred to as TBA) or methyl tert-butyl ether (hereinafter, referred to as MTBE) to gas phase catalytic oxidation using molecular oxygen to synthesize an unsaturated aldehyde and an unsaturated carboxylic acid. Further, the present invention relates to a catalyst produced by this method, and a method of synthesizing an unsaturated aldehyde and an unsaturated carboxylic acid using this catalyst.

BACKGROUND ART

Conventionally, there are a lot of suggestions on catalysts used in subjecting propylene, isobutylene, TBA or MTBE to gas phase catalytic oxidation to synthesize an unsaturated aldehyde and an unsaturated carboxylic acid, and on methods of producing the same.

The majority of such catalysts have a composition containing at least molybdenum, bismuth and iron, and industrially, a molding catalyst having such a composition is used. The molding catalysts are classified into extrusion molding catalysts, supporting molding catalysts and the like depending on their molding methods. The extrusion molding catalyst is produced usually via a process of kneading and extrusion-molding particles containing a catalyst component. On the other hand, the supporting molding catalyst is produced usually via a process of allowing a powder containing a catalyst component to be supported on a support.

Regarding the extrusion molding catalyst, there are suggested, for example, a method in which silica sol and inorganic fiber are added in production, for improvement of strength (Japanese Patent Application Laid-Open (JP-A) No. 9-52053), a method in which a certain kind of cellulose derivative is added in extrusion-molding a catalyst (JP-A No. 7-16464), and the like. However, catalysts obtained by these known methods are not necessarily sufficient as industrial catalysts from the standpoints of catalyst activity and selectivity of the intended product, and the like, and there is desired further improvement.

Besides, the above-mentioned JP-A No. 9-52053 describes that a mixture or kneaded substance of a catalyst component, silica sol and inorganic fiber is preserved by leaving it at room temperature for about 6 to 20 hours under conditions not causing evaporation of moisture (preserving treatment), before molding, to improve the mechanical strength of a molded catalyst. The reason for improvement in the strength of the molded body by preserving is described that by increase in the contact time of a catalyst component with water and the like, the catalyst component is disintegrated into near primary particles, and a molded article, when molded, becomes compact. However, preserving of a mixture or kneaded substance having no definite shape is not necessarily advantageous, and control of activity is difficult in some cases. Further, sufficient selectivity of the intended product is not necessarily obtained.

JP-A No. 2000-71313, Example 4 describes a method in which a clayey material obtained by kneading an isobutylene oxidation catalyst containing molybdenum, bismuth and iron is temporarily-molded into a cylinder, which is filled in a cylinder of a piston type extrusion molding machine, and extrusion-molded. However, in this method, a temporary-molded material in the form of cylinder and the final-molded product are not preserved, therefore, activity of the resulted catalyst may be low in some cases.

DISCLOSURE OF THE INVENTION

An object of the present invention is to provide a method of producing a catalyst for synthesis of an unsaturated aldehyde and unsaturated carboxylic acid, which can easily control catalytic activity and give a catalyst of high activity and high selectivity. Further, an object of the present invention is to provide a catalyst produced by this method, and a method of synthesizing an unsaturated aldehyde and unsaturated carboxylic acid at high yield using this catalyst.

The present invention relates to a method of producing an extrusion molding catalyst containing at least molybdenum, bismuth and iron, used in subjecting at least one of propylene, isobutylene, tert-butyl alcohol and methyl-tert-butyl ether to gas phase catalytic oxidation with molecular oxygen to synthesize an unsaturated aldehyde and unsaturated carboxylic acid, wherein the method comprises the steps of (i) adding liquid to particles containing molybdenum, bismuth and iron and kneading the mixture, and extrusion-molding this kneaded substance, (ii) preserving the molded article obtained by extrusion molding, and (iii) drying and/or calcining the preserved molded article, and time from addition of liquid to particles containing molybdenum, bismuth and iron to immediately before the step (iii), namely contact time of particles with liquid, is 1 to 48 hours, and time of preserving the molded article in the step (ii), namely preserving time, is 50% or more of the contact time of particles containing molybdenum, bismuth and iron with liquid.

Further, the present invention relates to a method of producing an extrusion molding catalyst containing at least molybdenum, bismuth and iron, used in subjecting at least one of propylene, isobutylene, tert-butyl alcohol and methyl-tert-butyl ether to gas phase catalytic oxidation with molecular oxygen to synthesize an unsaturated aldehyde and unsaturated carboxylic acid, wherein the method comprises the steps of (i) adding liquid to particles containing molybdenum, bismuth and iron and kneading the mixture, and molding, namely primary-molding, this kneaded substance, (ii) preserving the primary molded article obtained by molding, (iii) extrusion-molding, namely secondary-molding, the primary molded article preserved, and (iv) drying and/or calcining the secondary molded article obtained by extrusion molding, and time from addition of liquid to particles containing molybdenum, bismuth and iron to immediately before the step (iv), namely contact time of particles with liquid, is 1 to 48 hours, and time of preserving the primary molded article in the step (ii), namely preserving time, is 50% or more of the contact time of particles containing molybdenum, bismuth and iron with liquid.

Furthermore, the present invention relates to the above-mentioned method of producing a catalyst for synthesis of an unsaturated aldehyde and unsaturated carboxylic acid wherein, in the step of preserving the molded article or primary molded article, the preserving temperature is 3 to 40° C.

Still further, the present invention relates to a catalyst for synthesis of an unsaturated aldehyde and unsaturated carboxylic acid, produced by the above-mentioned method.

Even further, the present invention relates to a method of synthesizing an unsaturated aldehyde and unsaturated carboxylic acid wherein at least one of propylene, isobutylene, tert-butyl alcohol and methyl-tert-butyl ether are subjected to gas phase catalytic oxidation with molecular oxygen in the presence of the above-mentioned catalyst.

The phrase "containing molybdenum, bismuth and iron" means "containing molybdenum, bismuth and iron as metal elements", and it is estimated that this metal element is contained in the form of oxide or complex oxide.

Hereinafter, the phrase "particles containing molybdenum, bismuth and iron" is substituted also by "particles containing catalyst components".

BEST MODES FOR CARRYING OUT THE INVENTION

The catalyst obtained by the present invention contains at least molybdenum, bismuth and iron as catalyst components, and is used for subjecting reaction raw materials propylene, isobutylene, TBA or MTBE to gas phase catalytic oxidation with molecular oxygen to synthesize an unsaturated aldehyde and an unsaturated carboxylic acid. The reaction raw materials may be used singly or in combination of two or more of them.

Here, "unsaturated aldehyde and unsaturated carboxylic acid" means specifically acrolein or acrylic acid when the reaction raw material is propylene, and methacrolein and methacrylic acid in the case of other reaction raw materials. Depending on the catalyst composition and reaction conditions, either an unsaturated aldehyde or an unsaturated carboxylic acid is produced in some cases, and the present invention includes such cases.

The method of producing a catalyst for synthesizing an unsaturated aldehyde and unsaturated carboxylic acid comprises, as described above, the steps of (i) adding liquid to particles containing catalyst components and kneading the mixture, and extrusion-molding this kneaded substance, (ii) preserving the molded article obtained by extrusion molding, and (iii) drying and/or calcining the preserved molded article, or the steps of (i) adding liquid to particles containing catalyst components and kneading the mixture, and molding, namely primary-molding, this kneaded substance, (ii) preserving the primary molded article obtained by molding, (iii) extrusion-molding, namely secondary-molding, the primary molded article preserved, and (iv) at least one step of drying and calcining the secondary molded article obtained by extrusion molding, and controls the contact time of particles containing catalyst components with liquid from 1 to 48 hours by regulation of the preserving time of the molded article (also including primary molded article) and controls the preserving time of the molded article at 50% or more of the contact time of particles containing catalyst components with liquid. In the present invention, it is necessary that "preserving time of the molded article" is more than time other than "preserving time of the molded article" in "contact time of particles containing catalyst components with liquid", namely, more than the total time of times necessary for kneading and molding and the preserving time of a kneaded substance having no definite shape.

By thus controlling the contact time of particles containing catalyst components with liquid by regulation of the preserving time of the molded article, the activity of the resulted catalyst can be easily controlled, and a catalyst having excellent activity and showing excellent selectivity of the intended product can be obtained. Therefore, according to the present invention, a catalyst of high activity and high selectivity having uniform activity is obtained, and by use of this catalyst, an unsaturated aldehyde and an unsaturated carboxylic acid can be produced in high yield.

Though the reason for a fact that a catalyst of high activity and high selectivity having uniform activity is obtained is not apparent, it is supposed that by conducting preserving after molding in constant form, elution and diffusion of molybdenum, bismuth, iron and other catalyst components, particularly, alkali metals such as potassium, cesium and the like occur without localization during preserving, and these are rearranged without localization in the subsequent drying and calcination.

In the present invention, it is important that kneaded substances are all molded in constant form. By molding kneaded substances all in constant form, deviation of the activity of the resulted catalyst further decreases and reproducibility also increases.

Here, "preserving" indicates leaving of a catalyst molded article containing liquid before drying and calcination (also involving primary molded article) under condition causing difficult evaporation of the liquid. As the preserving method, a method in which a catalyst molded article (also including primary molded article) is wrapped by a plastic film, plastic sheet or the like, or placed in a closed vessel and left under condition suppressing evaporation of liquid, or other methods and the like are mentioned. "contact time of particles containing catalyst components (particles containing molybdenum, bismuth and iron) with liquid" indicates time from addition of liquid to particles containing catalyst components in kneading to immediately before a step of drying and/or calcining a molded article (also including secondary molded article). Further, here, "drying" indicates positive evaporation of liquid contained in a molded article such as air drying and hot air drying and the like. Calcination indicates heating treatment at high temperature in common use.

The catalyst for synthesis of an unsaturated aldehyde and an unsaturated carboxylic acid and the method of producing the same, according to the present invention, will be illustrated in detail below.

The catalyst of the present invention is an extrusion-molded catalyst containing as catalyst components at least molybdenum, bismuth and iron. As the catalyst component, in addition, silicon, cobalt, nickel, chromium, lead, manganese, calcium, magnesium, niobium, silver, barium, tin, tantalum, zinc, phosphorus, boron, sulfur, selenium, tellurium, cerium, tungsten, antimony, titanium, lithium, sodium, potassium, rubidium, cesium, thallium and the like may be contained. The catalyst (particles containing catalyst components) of the present invention is estimated as a complex oxide of molybdenum, bismuth, iron and other metal elements.

Such an extrusion-molded catalyst containing at least molybdenum, bismuth and iron is produced generally via (1) a step of producing particles containing catalyst components, (2) a step of kneading the resulted particles containing catalyst components, and the like, (3) a step of extrusion-molding the resulted kneaded substance, and (4) a step of drying and/or calcining (heat treating) the resulted molded article. In the present invention, before drying and/or calcining the molded article, namely, between the step (3) and the step (4), a step of preserving the molded article obtained by extrusion molding is further included. Further, in the present invention, it may also be permissible that molding, namely primary molding, is conducted once, and preserving is effected, then, molding, namely secondary molding, into the final shape is conducted.

In the present invention, the step (1) is not particularly restricted, and conventionally known various methods can be applied, and usually, an aqueous slurry containing at least molybdenum, bismuth and iron is dried, and if necessary, further ground to give particles.

The method of producing an aqueous slurry containing at least molybdenum, bismuth and iron is not particularly restricted, and providing there is no remarkable localization of components, conventionally well known various methods can be used such as a precipitation method, oxide mixing method and the like.

As the raw material of the catalyst component to be dissolved in an aqueous slurry, oxides, sulfates, nitrates, carbonates, hydroxides, ammonium salts, halides and the like of various elements can be used. For example, as the molybdenum raw material, ammonium p-molybdate, molybdenum trioxide and the like are listed. The raw materials of the catalyst components may be used singly or in combination of two or more for each element.

The method of drying an aqueous slurry to give particles is not particularly restricted, and there can be applied, for example, a method of drying using a spray drier, a method of drying using a slurry drier, a method of drying using a drum drier, a method of drying to solid by evaporation and grinding the dried substance in the form of bulk, and other methods. Of them, it is preferable to obtain dry particles in the form of sphere using a spray drier, since particles are obtained simultaneously with drying and since the form of the resulted particle is a regular shape suitable for the present invention. Though the drying conditions vary depending on the drying method, when a spray drier is used, the inlet temperature is usually from 100 to 500° C., the outlet temperature is usually 100° C. or more, preferably, from 105 to 200° C.

Thus obtained dry particles contain salts of nitric acid and the like derived from catalyst raw materials and the like in some cases, and when these salts are decomposed by calcination after molding, there is a possibility of decrease in the strength of a molded article. For this reason, it is preferable that particles are not only dried, but also calcined in this stage to give calcined particles. The calcination conditions are not particularly restricted, and known calcination conditions can be applied. Usually, calcination is conducted in a temperature range of from 200 to 600° C., and the calcination time is appropriately selected depending on the intended catalyst.

The average particle diameter of dry particles or calcined particles containing catalyst components used for molding is preferably 10 μm or more, further preferably 20 μm or more, particularly preferably 45 μm or more. When the average particle diameter of particles containing catalyst components increases, there is a tendency that a large void, namely, a large pore is formed between particles after molding, to increase selectivity. The average particle diameter of dry particles or calcined particles containing catalyst components used for molding is preferably 150 μm or less, further preferably 100 μm or less, particularly preferably 65 μm or less. When the average particle diameter of particles containing catalyst components decreases, the number of contact points between particles per unit volume increases, therefore, there is a tendency of increase in the mechanical strength of the resulted catalyst molded article.

The bulk density of particles containing catalyst components is preferably 0.5 kg/L or more, further preferably 0.8 kg/L or more, from the standpoint of handling. The bulk density of particles containing catalyst components is preferably 1.8 kg/L or less, further preferably 1.2 kg/L or less, from the standpoint of performance.

The strength of particles containing catalyst components is preferably $9.8 \times 10^{-4}$ N or more since when the strength is small, particles are broken in molding, leading to little effective pore. On the other hand, the strength of particles containing catalyst components is preferably $9.8 \times 10^{-2}$ N or less since when the strength is large, selectivity decreases in some cases.

Next, in the step (2), a mixture of particles obtained in the step (1) and liquid is kneaded.

The apparatus used for kneading is not particularly restricted, and for example, a batch-wise kneader using a double arm type stirring blade, continuous kneaders of axis rotation reciprocation mode, self cleaning mode and the like, can be used. Of them, batch-wise apparatuses are preferable since kneading can be conducted while confirming the condition of the kneaded substance. The termination of kneading is usually judged temporally, visually or by manual touch.

As the liquid used in the step (2), water and alcohols are preferable. As such alcohols, for example, lower alcohols such as ethanol, methyl alcohol, propyl alcohol, butyl alcohol and the like are listed. Of them, water is particularly preferable from the standpoints of economy and handling. These liquids may be used singly or in combination of two or more.

The use amount of liquid is appropriately selected depending on the kind and size of particles, the kind of liquid, and the like, and usually, it is from 10 to 70 parts by weight based on 100 parts by weight of particles containing catalyst components obtained in the step (1). The use amount of liquid is preferably 20 parts by weight or more, further preferably 30 parts by weight or more, particularly preferably 35 parts by weight or more based on 100 parts by weight of particles containing catalyst components. When the use amount of liquid increases, there is a tendency that a large void, namely, a large pore is formed in the dried and calcined molded article (extrusion-molded catalyst of the present invention) to increase selectivity. On the other hand, the use amount of liquid is preferably 60 parts by weight or less, further preferably 50 parts by weight or less, particularly preferably 45 parts by weight or less based on 100 parts by weight of particles containing catalyst components. When the use amount of liquid decreases, there is a tendency that adhesion in molding lowers and handling increases, and the molded article becomes more compact, leading to increase in the strength of the molded article.

In the step (2), further, it is preferable to add a molding auxiliary such as an organic binder and the like. By addition of a molding auxiliary, the strength of the resulted molded article increases. As such a molding auxiliary, for example, methylcellulose, ethylcellulose, carboxymethylcellulose, carboxymethylcellulosesodium, hydroxyethylcellulose, hydroxypropylcellulose, hydroxypropylmethylcellulose, hydroxyethylmethylcellulose, hydroxybutylmethylcellulose, ethylhydroxyethylcellulose, hydroxypropylcellulose and the like are listed. These molding auxiliaries may be used singly or in combination of two or more. It is usual that the addition amount of the molding auxiliary is preferably 0.1 part by weight or more, particularly preferably 2 parts by weight or more based on 100 parts by weight of particles containing catalyst components. Further, it is usual that the addition amount of the molding auxiliary is preferably 10 parts by weight or less, particularly preferably 6 parts by weight or less based on 100 parts by weight of particles containing catalyst components since then post treatments such as heat treatment after molding and the like become easy.

Further, in the step (2), conventionally known additives other than the above-mentioned auxiliaries may be used. As such additives, for example, inorganic compounds such as graphite, diatomaceous earth and the like, inorganic fibers such as glass fiber, ceramic fiber, carbon fiber and the like, and so on are listed.

In the step (3), the kneaded substance obtained in the step (2) is extrusion-molded. Though this molding may be molding into the final intended shape, primary molding is preferable from the standpoint of productivity.

As the primary molding method, for example, extrusion molding and press molding are listed. Of them, extrusion molding is preferable, and more preferable is extrusion molding using a screw type extruder from the standpoint of productivity. Further, the kneading step (2) and the extrusion molding step (3) may be carried out continuously, and they may also be conducted simultaneously using an integrated type apparatus suitable for this.

The form of the primary molded article is not particularly restricted, and for example, cylinder, rectangular parallelopiped, cube and the like are selected. Also the size of the molded article is not particularly restricted, and size of certain level or more is preferable since reproducibility tends to increase when the size is larger. For example, the size of the thinnest portion of the primary molded article is preferably 10 mm or more, further preferably 30 mm or more.

In the present invention, after primary molding, the primary molded article is preserved, and the contact time of particles containing catalyst components with liquid is controlled. When preserving at the final intended form is possible, shaping into the final intended form is conducted without effecting the primary molding, then, the molded article is preserved.

Preserving is conducted by wrapping a molded article with a plastic film, plastic sheet or the like and/or placing a molded article into a closed vessel, and leaving it for given time at given temperature under condition suppressing evaporation of liquid. Particularly, it is preferable that a molded article is wrapped with a plastic film, plastic sheet or the like so as to produce no clearance, to realize sealing, and it is more preferable that thus sealed article is further place in a closed vessel for sealing.

As described above, it is necessary that "preserving time of the molded article" is more than time other than "preserving time of the molded article" in "contact time of particles containing catalyst components with liquid", namely, more than the total time of times necessary for kneading and molding and the preserving time of a kneaded substance having no definite shape. Namely, the ratio of "preserving time of the molded article" is 50% or more, preferably 70% or more, further preferably 80% or more, particularly preferably 90% or more in "contact time of particles containing catalyst components with liquid".

In the present invention, the contact time of particles containing catalyst components with liquid is from 1 to 48 hours. The contact time of particles containing catalyst components with liquid is preferably 3 hours or more, further preferably 8 hours or more, particularly preferably 20 hours or more. When the contact time of particles containing catalyst components with liquid is longer, the resulted catalyst tends to have higher activity and also improved reproducibility. The contact time of particles containing catalyst components with liquid is preferably 36 hours or less, further preferably 30 hours or less, particularly preferably 27 hours or less. When the contact time of particles containing catalyst components with liquid is shorter, the resulted catalyst tends to have improved selectivity.

During this period, the preserving time of the molded article is preferably 0.5 hours or more, further preferably 1 hour or more, particularly preferably 6 hours or more, more preferably 18 hours or more. On the other hand, the preserving time of the molded article is preferably 46 hours or less, further preferably 34 hours or less, particularly preferably 28 hours or less, more preferably 25 hours or less.

The preserving temperature is usually from 3 to 40° C. The preserving temperature is preferably 10° C. or more, further preferably 15° C. or more. When the preserving temperature is higher, the resulted catalyst tends to have increased activity. The preserving temperature is preferably 35° C. or less, further preferably 30° C. or less. When the preserving temperature is lower, the molded article tends to show decreased adhesion and improved handling.

Preserving is not necessarily required to be conducted at constant temperature, and the preserving temperature may be changed in the above-mentioned temperature range, and when conducted at constant temperature, control of activity and the like is easy.

It becomes possible to control the activity of the resulted catalyst, by regulation of the contact time of particles containing catalyst components with liquid and the preserving time. The preserving time and temperature of the molded article may be appropriately selected depending on the activity of a catalyst powder and the activity of the intended molded article.

When the primary molded article is preserved, molding, namely secondary molding, into the final intended shape is effected after preserving.

The method of secondary molding is not particularly restricted, and for example, it may be conducted using an auger type extrusion molding machine, piston type extrusion molding machine and the like.

The form of the secondary molded article is not particularly restricted, and molding into any shape such as ring, cylinder, star and the like is possible. The present invention is suitable when the secondary molded article is in the form of ring, particularly, ring having a diameter of 15 mm or less. "Ring form" is alternatively called "hollow cylinder form".

In the primary molding and secondary molding, namely final molding, it is preferable not to conduct vacuum deaeration so as not to decrease the pore volume of a catalyst.

Next, in the step (4), a catalyst molded article is dried and/or calcined to give a catalyst, namely product.

The drying method is not particularly restricted, and generally known methods such as hot air drying, humidity drying, far infrared drying, micro wave drying and the like can be optionally used. The drying condition may be appropriately selected depending on the intended water content.

Though the dry molded article is usually calcined, when particles are calcined in the step (1) and an organic binder and the like are not used, it is also possible to omit calcination. The calcination conditions are not particularly restricted, and known calcination conditions can be applied. Usually, calcination is conducted at temperatures in a temperature range of from 200 to 600° C., and the calcination time is appropriately selected depending on the intended catalyst.

It may be also permissible that the drying step is omitted, and calcination is only conducted.

The catalyst containing at least molybdenum, bismuth and iron produced in the present invention preferably has a composition of the following general formula (I).

$$Mo_aBi_bFe_cM_dX_eY_fZ_gSi_hO_i \qquad (I)$$

In the formula (I), Mo, Bi, Fe, Si and O represent molybdenum, bismuth, iron, silicon and oxygen, respectively, and M represents at least one element selected from the group consisting of cobalt and nickel, X represents at least one element selected from the group consisting of chromium, lead, manganese, calcium, magnesium, niobium, silver, barium, tin, tantalum and zinc, Y represents at least one element selected from the group consisting of phosphorus, boron, sulfur, selenium, tellurium, cerium, tungsten, antimony and titanium, and Z represents at least one element selected from the group consisting of lithium, sodium, potassium, rubidium, cesium and thallium.

a, b, c, d, e, f, g, h and i represent atomic ratios of elements, and when a=12, then, b=0.01 to 3, c=0.01 to 5, d=1 to 12, e=0 to 8, f=0 to 5, g=0.01 to 2, and h=0 to 20, and i represents an oxygen atomic ratio necessary for satisfying the above-mentioned atomic valences of components.

In the present invention, conventionally known inorganic compounds such as graphite, diatomaceous earth and the like, inorganic fibers such as glass fiber, ceramic fiber, carbon fiber and the like, and so on can be added. Addition thereof may be conducted in kneading of the step (2).

Next, the method of synthesizing an unsaturated aldehyde and an unsaturated carboxylic acid of the present invention will be illustrated.

In the method of synthesizing an unsaturated aldehyde and an unsaturated carboxylic acid of the present invention, a raw material gas containing any one or more of reaction raw materials, propylene, isobutylene, TBA and MTBE, and molecular oxygen is subjected to gas phase catalytic oxidation in the presence of a catalyst produced by the method of the present invention.

The reaction is usually conducted in a fixed bed. One catalyst layer may be used or two or more catalyst layers may be used.

In this case, in a reaction tube, a catalyst may be diluted with inert carriers such as silica, alumina, silica-alumina, silicon carbide, titania, magnesia, ceramic ball, stainless steel and the like. Further, these inert carriers may be added also in the step (2), namely, in kneading.

The concentration of reaction raw materials, propylene, isobutylene, TBA and MTB, in a raw material gas can be varied in the wide range, and preferably is from 1 to 20 vol %.

Though it is economical to use air as a molecular oxygen source, air enriched with oxygen, and the like may also be used, if necessary. The molar ratio of reaction raw materials to oxygen in the raw material gas, namely volume ratio, is preferably in a range from 1:0.5 to 1:3.

It is preferable that the raw material gas contains water in addition to reaction raw materials and molecular oxygen, and it is preferable that the raw material gas is diluted with an inert gas such as nitrogen, carbon dioxide and the like. The concentration of water in the raw material gas is preferably from 1 to 45 vol %.

The reaction pressure is preferably from normal pressure to several hundred kPa. The reaction temperature is selected usually in a range from 200 to 450° C., preferably from 250 to 400° C. The contact time is preferably from 1.5 to 15 seconds.

EXAMPLES

The present invention will be specifically illustrated by the following examples and comparative examples.

Parts in the examples and comparative examples are by weight. For kneading, a batch-wise kneader equipped with a double arm type stirring blade was used. Analysis of a raw material gas and a reaction gas was conducted by gas chromatography. The catalyst composition was determined from the use amounts of catalyst raw materials.

The reaction ratio of raw material olefins, TBA and MTBE (hereinafter, referred to as reactivity), the selectivity of an unsaturated aldehyde and an unsaturated carboxylic acid produced, and the total yield of the unsaturated aldehyde and unsaturated carboxylic acid, in the examples and comparative examples, were calculated according to the following formulae.

Reactivity (%)=$A/B$×100

Selectivity (%) of unsaturated aldehyde=$C/A$×100

Selectivity (%) of unsaturated carboxylic acid=$D/A$×100

Total yield (%)=$(C+D)/B$×100

Here, A represents the mol number of raw material olefins, TBA or MTBE reacted, B represents the mol number of raw material olefins, TBA or MTBE fed, C represents the mol number of an unsaturated aldehyde produced, and D represents the mol number of an unsaturated carboxylic acid produced.

Example 1

To 1000 parts of pure water was added 500 parts of ammonium p-molybdate, 12.4 parts of ammonium p-tungstate, 23.0 parts of cesium nitrate, 27.4 parts of antimony trioxide and 33.0 parts of bismuth trioxide, and they were stirred with heating (solution A). Separately, to 1000 parts of pure water was added 209.8 parts of ferric nitrate, 75.5 parts of nickel nitrate, 453.3 parts of cobalt nitrate, 31.3 parts of lead nitrate and 5.6 parts of 85% phosphoric acid, sequentially, and they were dissolved (solution B). The solution B was added to the solution A to give an aqueous slurry, then, this aqueous slurry was made into dry particles in the form of sphere having an average particle size of 60 µm using a spray drier. The dry spherical particles were calcined at 300° C. for 1 hour then at 510° C. for 3 hours, to give a catalyst calcined substance. Thus obtained catalyst calcined substance had an average particle size of 55 µm, a particle strength of 1.3×10⁻² N and a bulk density of 0.95 kg/L.

To 500 parts of thus obtained catalyst calcined substance was added 15 parts of methylcellulose, and these were dry-mixed. Into this was mixed 180 parts of pure water, and these were mixed (kneaded) by a kneader to give a clayey substance, then, the kneaded substance having no definite shape was extrusion-molded using a screw type extrusion molding machine, to obtain a primary molded article in the form of cylinder having a diameter of 45 mm and a length of 280 mm, namely primary molding. In molding, vacuum deaeration was not conducted.

Then, this primary molded article was sealed by wrapping with a plastic film so as not to allow evaporation of water, further, placed in a closed vessel and preserved in a constant temperature chamber of 25° C. for 22 hours. After preserving, this primary molded article was extrusion-molded using a piston type extrusion molding machine, to obtain a catalyst molded article in the form of ring having an outer diameter of 5 mm, an inner diameter of 2 mm and a length of 5 mm, namely secondary molding. In molding, vacuum deaeration was not conducted.

Next, the resulted catalyst molded article was dried using a 110° C. hot air drier, and calcined again at 400° C. for 3 hours, to give a final calcined article of the catalyst molded article. In this operation, the contact time of particles containing catalyst components with water was 24 hours.

The composition of elements other than oxygen in the resulted catalyst molded article is as described below.

$Mo_{12}W_{0.2}Bi_{0.6}Fe_{2.2}Sb_{0.8}Ni_{1.1}Co_{6.6}Pb_{0.4}P_{0.2}Cs_{0.5}$

This catalyst molded article was filled in a stainless reaction tube, and reaction was conducted using a raw material gas containing 5% of isobutylene, 12% of oxygen, 10% of water vapor and 73% of nitrogen (all vol %) under normal pressure at a reaction temperature of 340° C. for a contact time of 3.6 seconds. As a result of the reaction, the reactivity of isobutylene was 98.1%, the selectivity of methacrolein was 89.9%, and the selectivity of methacrylic acid was 4.0%.

Example 2

A catalyst molded article was produced and reaction was conducted in the same manner as in Example 1 except that the preserving time was 7 hours and the contact time of particles containing catalyst components with water was 8 hours. As a result of the reaction, the reactivity of isobutylene was 97.2%, the selectivity of methacrolein was 90.0%, and the selectivity of methacrylic acid was 4.0%.

Example 3

A catalyst molded article was produced and reaction was conducted in the same manner as in Example 1 except that the temperature of the constant temperature chamber was 35° C. As a result of the reaction, the reactivity of isobutylene was 98.2%, the selectivity of methacrolein was 89.7%, and the selectivity of methacrylic acid was 3.8%.

Example 4

A catalyst molded article was produced and reaction was conducted in the same manner as in Example 1 except that the temperature of the constant temperature chamber was 5° C. As a result of the reaction, the reactivity of isobutylene was 97.6%, the selectivity of methacrolein was 89.9%, and the selectivity of methacrylic acid was 4.0%.

Comparative Example 1

A catalyst molded article was produced and reaction was conducted in the same manner as in Example 1 except that, without conducting the primary molding, the kneaded substance having no definite shape was sealed by wrapping with a plastic film, further, placed in a closed vessel and preserved for 22 hours in a constant temperature chamber at 25° C., then, this kneaded substance was extrusion-molded using a piston type extrusion molding machine, to obtain a catalyst molded article in the form of ring having an outer diameter of 5 mm, an inner diameter of 2 mm and a length of 5 mm. In this operation, the contact time of particles containing catalyst components with water was 24 hours. As a result of the reaction, the reactivity of isobutylene was 97.6%, the selectivity of methacrolein was 89.4%, and the selectivity of methacrylic acid was 3.3%.

In comparison with Examples 1 to 4, irregularity in activity among the produced catalyst molded articles increased.

Comparative Example 2

A catalyst molded article was produced and reaction was conducted in the same manner as in Example 1 except that preserving of the primary molded article was not conducted. In this operation, the contact time of particles containing catalyst components with water was 40 minutes. As a result of the reaction, the reactivity of isobutylene was 97.2%, the selectivity of methacrolein was 89.6%, and the selectivity of methacrylic acid was 3.5%.

In comparison with Examples 1 to 4, irregularity in activity among the produced catalyst molded articles increased.

The results of Examples 1 to 4, and comparative Examples 1, 2 are summarized in Table 1.

TABLE 1

| | | Preserving | | | | Reaction result | | | |
|---|---|---|---|---|---|---|---|---|---|
| | Timing of preserving | Preserving temperature (° C.) | Preserving time (h) | Ratio of preserving time of molded article (%) | Contact time with liquid (h) | Reactivity (%) | Aldehyde selectivity (%) | Carboxylic acid selectivity (%) | Total yield (%) |
| Example 1 | Primary molded article | 25 | 22 | 91.7 | 24 | 98.1 | 89.9 | 4.0 | 92.1 |
| Example 2 | Primary molded article | ditto | 7 | 85.7 | 8 | 97.2 | 90.0 | 4.0 | 91.4 |
| Example 3 | Primary molded article | 35 | 22 | 91.7 | 24 | 98.2 | 89.7 | 3.8 | 91.8 |
| Example 4 | Primary molded article | 5 | 22 | 91.7 | 24 | 97.6 | 89.9 | 4.0 | 91.6 |
| Comparative Example 1 | Kneaded substance | 25 | 22 | 91.7 | 24 | 97.6 | 89.4 | 3.3 | 90.5 |
| Comparative Example 2 | — | — | — | 0 | 40 min. | 97.2 | 89.5 | 3.5 | 90.4 |

Example 5

To 1000 parts of pure water was added 500 parts by ammonium p-molybdate, 6.2 parts of ammonium p-tungstate and 23.0 parts of cesium nitrate, and they were stirred with heating (solution A). Separately, to 600 parts of pure water was added 41.9 parts of 60 wt % nitric acid, and the mixture was made uniform, then, 68.7 parts of bismuth nitrate was added and dissolved. To this was added 200.2 parts of ferric nitrate, 116.6 parts of nickel nitrate, 432.7 parts of cobalt nitrate and 54.5 parts of magnesium nitrate, sequentially, further, 400 parts of water was added and they were dissolved (solution B). The solution B was added to the solution A to give an aqueous slurry, then, 24.1 parts of antimony trioxide was added and the mixture was stirred with heating, and dried using a spray drier to give dry particles in the form of sphere having an average particle size of 55 µm. The dry spherical particles were calcined at 300° C. for 1 hour then at 510° C. for 3 hours, to give a catalyst calcined substance. Thus obtained catalyst calcined substance had an average particle size of 51 µm, a particle strength of $1.7 \times 10^{-2}$ N and a bulk density of 0.96 kg/L.

To 500 parts of thus obtained catalyst calcined substance was added 15 parts of hydroxypropylmethylcellulose, and these were dry-mixed. Into this was mixed 170 parts of pure water, and these were mixed (kneaded) by a kneader to give a clayey substance, then, the kneaded substance having no definite shape was extrusion-molded using a screw type extrusion molding machine, to obtain a primary molded article in the form of cylinder having a diameter of 45 mm and a length of 280 mm, namely primary molding. In molding, vacuum deaeration was not conducted.

Then, this primary molded article was sealed by wrapping with a plastic film so as not to allow evaporation of water, further, placed in a closed vessel and preserved in a constant temperature chamber of 25° C. for 22 hours. After preserving, this primary molded article was extrusion-molded using a piston type extrusion molding machine, to obtain a catalyst molded article in the form of ring having an outer diameter of 5 mm, an inner diameter of 2 mm and a length of 5 mm, namely secondary molding. In molding, vacuum deaeration was not conducted.

Next, the resulted catalyst molded article was dried using a 110° C. hot air drier, and calcined again at 400° C. for 3 hours, to give a final calcined article of the catalyst molded article. In this operation, the contact time of particles containing catalyst components with water was 24 hours.

The composition of elements other than oxygen in the resulted catalyst molded article is as described below.

$Mo_{12}W_{0.1}Bi_{0.6}Fe_{2.1}Sb_{0.7}Ni_{1.7}Co_{6.3}Mg_{0.9}Cs_{0.5}$

This catalyst molded article was filled in a stainless reaction tube, and reaction was conducted using a raw material gas containing 5% of TBA, 12% of oxygen, 10% of water vapor and 73% of nitrogen (all vol %) under normal pressure at a reaction temperature of 340° C. for a contact time of 3.6 seconds. As a result of the reaction, the reactivity of TBA was 100%, the selectivity of methacrolein was 88.3%, and the selectivity of methacrylic acid was 2.5%.

Example 6

A catalyst molded article was produced and reaction was conducted in the same manner as in Example 5 except that the preserving time was 1 hour and 15 minutes. In this operation, the contact time of particles containing catalyst components with water was 2 hours. As a result of the reaction, the reactivity of TBA was 100%, the selectivity of methacrolein was 88.1%, and the selectivity of methacrylic acid was 2.3%.

Comparative Example 3

A catalyst molded article was produced and reaction was conducted in the same manner as in Example 5 except that, without conducting the primary molding, the kneaded substance having no definite shape was sealed by wrapping with a plastic film, further, placed in a closed vessel and preserved for 22 hours in a constant temperature chamber at 25° C., then, this kneaded substance was extrusion-molded using a piston type extrusion molding machine, to obtain a catalyst molded article in the form of ring having an outer diameter of 5 mm, an inner diameter of 2 mm and a length of 5 mm. In this operation, the contact time of particles containing catalyst components with water was 24 hours. As a result of the reaction, the reactivity of TBA was 100%, the selectivity of methacrolein was 87.5%, and the selectivity of methacrylic acid was 2.1%.

In comparison with Examples 5, 6, irregularity in activity among the produced catalyst molded articles increased.

The results of Examples 5 and 6 and comparative Example 3 are summarized in Table 2.

TABLE 2

| | | Preserving | | | | Reaction result | | | |
| --- | --- | --- | --- | --- | --- | --- | --- | --- | --- |
| | Timing of preserving | Preserving temperature (° C.) | Preserving time (h) | Ratio of preserving time of molded article (%) | Contact time with liquid (h) | Reactivity (%) | Aldehyde selectivity (%) | Carboxylic acid selectivity (%) | Total yield (%) |
| Example 5 | Primary molded article | 25 | 22 | 91.7 | 24 | 100.0 | 88.3 | 2.5 | 90.8 |
| Example 6 | Primary molded article | 25 | 1 h 15 min. | 62.5 | 2 | 100.0 | 88.1 | 2.3 | 90.4 |
| Comparative Example 3 | Kneaded substance | 25 | 22 | — | 24 | 100.0 | 87.5 | 2.1 | 89.6 |

Example 7

To 1000 parts of pure water was added 500 parts by ammonium p-molybdate, 6.2 parts of ammonium p-tungstate, 1.4 parts of potassium nitrate, 27.5 parts of antimony trioxide and 49.5 parts of bismuth trioxide, and they were stirred with heating (solution A). Separately, to 1000 parts of pure water was added 123.9 parts of ferric nitrate, 288.4 parts of cobalt nitrate and 28.1 parts of zinc nitrate, sequentially, and they were dissolved (solution B). The solution B was added to the solution A to give an aqueous slurry, then, this aqueous slurry was dried using a spray drier to give dry particles in the form of sphere having an average particle size of 60 μm. The dry spherical particles were calcined at 300° C. for 1 hour, to give a catalyst calcined substance. Thus obtained catalyst calcined substance had an average particle size of 54 μm, a particle strength of $1.1 \times 10^{-2}$ N and a bulk density of 0.90 kg/L.

To 500 parts of thus obtained catalyst calcined substance was added 15 parts of methylcellulose, and these were dry-mixed. Into this was mixed 185 parts of pure water, and these were mixed (kneaded) by a kneader to give a clayey substance, then, the kneaded substance having no definite shape was molded using a screw type extrusion molding machine and a pill machine, to obtain a primary molded article in the form of sphere having a diameter of 20 mm, namely primary molding. In molding, vacuum deaeration was not conducted.

Then, this primary molded article was sealed by wrapping with a plastic film so as not to allow evaporation of water, further, placed in a closed vessel and preserved in a constant temperature chamber of 18° C. for 28 hours. After preserving, this primary molded article was extrusion-molded using a screw type extrusion molding machine, to obtain a catalyst molded article in the form of ring having an outer diameter of 5 mm, an inner diameter of 2 mm and a length of 5 mm, namely secondary molding. In molding, vacuum deaeration was not conducted.

Next, the resulted catalyst molded article was dried using a 110° C. hot air drier, and calcined again at 510° C. for 3 hours, to give a final calcined article of the catalyst molded article. In this operation, the contact time of particles containing catalyst components with water was 30 hours.

The composition of elements other than oxygen in the resulted catalyst molded article is as described below.

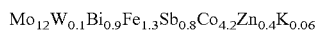

$Mo_{12}W_{0.1}Bi_{0.9}Fe_{1.3}Sb_{0.8}Co_{4.2}Zn_{0.4}K_{0.06}$

This catalyst molded article was filled in a stainless reaction tube, and reaction was conducted using a raw material gas containing 5% of propylene, 12% of oxygen, 10% of water vapor and 73% of nitrogen (all vol %) under normal pressure at a reaction temperature of 310° C. for a contact time of 3.6 seconds. As a result of the reaction, the reactivity of propylene was 99.0%, the selectivity of acrolein was 91.0%, and the selectivity of acrylic acid was 6.5%.

Example 8

A catalyst molded article was produced and reaction was conducted in the same manner as in Example 7 except that the kneaded substance having no definite shape was extrusion-molded using a screw type extrusion molding machine, to obtain a catalyst molded article in the form of ring having an outer diameter of 5 mm, an inner diameter of 2 mm and a length of 5 mm, and this molded article was sealed by wrapping with a plastic film, further, placed in a closed vessel and preserved for 28 hours in a constant temperature chamber at 28° C. In this operation, the contact time of particles containing catalyst components with water was 30 hours. As a result of the reaction, the reactivity of propylene was 99.0%, the selectivity of acrolein was 90.8%, and the selectivity of acrylic acid was 6.4%.

Example 9

A catalyst molded article was produced and reaction was conducted in the same manner as in Example 7 except that, before primary molding, the kneaded substance having no definite shape was sealed by wrapping with a plastic film, further, placed in a closed vessel and preserved for 12 hours in a constant temperature chamber at 18° C., and the primary molded article was sealed by wrapping with a plastic film and preserved for 16 hours in a constant temperature chamber at 18° C. In this operation, the contact time of particles containing catalyst components with water was 30 hours. As a result of the reaction, the reactivity of propylene was 98.8%, the selectivity of acrolein was 90.7%, and the selectivity of acrylic acid was 6.4%.

Comparative Example 4

A catalyst molded article was produced and reaction was conducted in the same manner as in Example 7 except that, without conducting the primary molding, the kneaded substance having no definite shape was sealed by wrapping with a plastic film, further, placed in a closed vessel and preserved for 28 hours in a constant temperature chamber at 18° C., then, this kneaded substance was extrusion-molded using a piston type extrusion molding machine, to obtain a catalyst molded article in the form of ring having an outer diameter of 5 mm, an inner diameter of 2 mm and a length of 5 mm. In this operation, the contact time of particles containing catalyst components with water was 30 hours. As a result of the reaction, the reactivity of propylene was 98.8%, the selectivity of acrolein was 90.1%, and the selectivity of acrylic acid was 6.0%.

In comparison with Examples 7 to 9, irregularity in activity among the produced catalyst molded articles increased.

The results of Examples 7 to 9 and Comparative Example 4 are summarized in Table 3.

TABLE 3

| | Timing of preserving | Preserving temperature (° C.) | Preserving time (h) | Ratio of preserving time of molded article (%) | Contact time with liquid (h) | Reactivity (%) | Aldehyde selectivity (%) | Carboxylic acid selectivity (%) | Total yield (%) |
|---|---|---|---|---|---|---|---|---|---|
| Example 7 | Primary molded article | 18 | 28 | 86.7 | 30 | 99.0 | 91.0 | 6.5 | 96.5 |
| Example 8 | Final molded article | 18 | 28 | 86.7 | 30 | 99.0 | 90.8 | 6.4 | 96.2 |
| Example 9 | Kneaded substance Primary molded article | 18 | 12 + 16 | 53.3 | 30 | 98.8 | 90.7 | 6.4 | 95.9 |
| Comparative Example 4 | Kneaded substance | 18 | 28 | — | 30 | 98.8 | 90.1 | 6.0 | 94.9 |

INDUSTRIAL APPLICABILITY

The catalyst for synthesis of an unsaturated aldehyde and an unsaturated carboxylic acid which is obtained by the present invention is excellent in catalytic activity and in selectivity of the intended product. Therefore, by using this catalyst, an unsaturated aldehyde and an unsaturated carboxylic acid can be produced with good yield. Further, according to the method of producing a catalyst for synthesis of an unsaturated aldehyde and an unsaturated carboxylic acid of the present invention, catalytic activity can be easily controlled.

What is claimed is:

1. A method of producing an extrusion molding catalyst comprising molybdenum, bismuth and iron, used for the catalytic gas phase oxidation of at least one of propylene, isobutylene, tert-butyl alcohol and methyl-tert-butylether with molecular oxygen, to form at least one of an unsaturated aldehyde and an unsaturated carboxylic acid, the method comprising:
   drying an aqueous slurry containing molybdenum, bismuth and iron to form dried particles in the form of a sphere;
   calcining the dried particles at a temperature of from 200 to 600° C. to form calcined particles;
   adding a liquid to the calcined particles comprising molybdenum, bismuth and iron, to form a first mixture;
   kneading the first mixture to form a kneaded mixture;
   carrying out a primary molding of the kneaded mixture to form a molded article, wherein the primary molding is extrusion molding;
   preserving the molded article for a preserving time;
   extrusion molding the molded article to form an extrusion molded article; and
   drying, calcining or both drying and calcining the extrusion molded article;
   wherein the time from adding the liquid to the calcined particles to immediately before the drying, the calcining or the both drying and the calcining of the preserved molded article is from 1 to 48 hours, and
   wherein the preserving time is a period of time that is 50% or more of the period of time which the particles are in contact with the liquid.

2. The method according to claim 1, wherein the preserving is carried out at a temperature of from 3 to 40° C.

3. The method according to claim 1, wherein the liquid is water.

4. The method according to claim 1, wherein from 10-70 parts by weight of liquid are added to the particles, wherein parts by weight is based on 100 parts by weight of the particles.

5. A catalyst produced by the method of claim 1.

6. The method according to claim 1, wherein the calcining decomposes a nitrate present in the dried particles.

7. A catalyst produced by the method of claim 2.

8. A catalyst produced by the method of claim 3.

9. A catalyst produced by the method of claim 4.

* * * * *